US012697175B2

(12) United States Patent (10) Patent No.: US 12,697,175 B2
Köstler (45) Date of Patent: Aug. 4, 2026

(54) METHOD FOR INSTRUMENT CALIBRATION UPDATE

(71) Applicant: Brainlab SE, Munich (DE)

(72) Inventor: Martin Köstler, Munich (DE)

(73) Assignee: Brainlab SE, Munich (DE)

( * ) Notice: Subject to any disclaimer, the term of this patent is extended or adjusted under 35 U.S.C. 154(b) by 392 days.

(21) Appl. No.: 18/269,025

(22) PCT Filed: Jan. 15, 2021

(86) PCT No.: PCT/EP2021/050761
§ 371 (c)(1),
(2) Date: Jun. 22, 2023

(87) PCT Pub. No.: WO2022/152388
PCT Pub. Date: Jul. 21, 2022

(65) Prior Publication Data
US 2024/0074815 A1      Mar. 7, 2024

(51) Int. Cl.
*A61B 34/20* (2016.01)
*A61B 90/00* (2016.01)
(52) U.S. Cl.
CPC .............. *A61B 34/20* (2016.02); *A61B 90/39* (2016.02); *A61B 2034/2065* (2016.02); *A61B 2090/3937* (2016.02)
(58) Field of Classification Search
CPC . A61B 34/20; A61B 90/39; A61B 2034/2065; A61B 2090/3937; A61B 2017/00725; A61B 2034/2055; A61B 2090/3983
See application file for complete search history.

(56) References Cited

U.S. PATENT DOCUMENTS

| | | | |
|---|---|---|---|
| 6,434,507 B1 | 8/2002 | Clayton et al. | |
| 7,809,184 B2 | 10/2010 | Neubauer et al. | |
| 9,002,432 B2 | 4/2015 | Feilkas | |
| 10,624,702 B2 | 4/2020 | Moctezuma et al. | |
| 2008/0267531 A1 | 10/2008 | Satoh et al. | |
| 2009/0171197 A1 | 7/2009 | Burger et al. | |
| 2018/0140223 A1 | 5/2018 | Kheradpir et al. | |
| 2020/0100847 A1 | 4/2020 | Siegler et al. | |
| 2021/0007811 A1* | 1/2021 | Troxell .............. | A61B 17/1671 |

FOREIGN PATENT DOCUMENTS

WO        2019152730 A1      8/2019

OTHER PUBLICATIONS

International Search Report and Written Opinion for PCT/EP2021/050761, Date of Mailing Oct. 12, 2021, 14 pages.
Office Action received in corresponding EP Application No. 21702167.4, mailed Dec. 3, 2024, 6 pages.

* cited by examiner

*Primary Examiner* — Jason M Ip
(74) *Attorney, Agent, or Firm* — Tucker Ellis LLP

(57) ABSTRACT

A computer-implemented method updates a calibration of a multi-component medical system, wherein a modified spatial relation between a first and a second section of interest of a modified system setup is determined as a function of an initial spatial relation between a first and a second section of interest of an initial system setup, particularly wherein at least one component of the initial setup of the medical system may remain in the modified setup of the medical system.

9 Claims, 3 Drawing Sheets

METHOD FOR INSTRUMENT CALIBRATION UPDATE

RELATED APPLICATION DATA

This application is a National Phase application of International Application No. PCT/EP2021/050761, filed Jan. 15, 2021, the contents of which are incorporated herein by reference.

FIELD

The present invention relates to a computer-implemented method of updating a calibration of a multi-component medical system or instrument, a corresponding computer program, a computer-readable storage medium storing such a program and a computer executing the program, as well as a medical system comprising an electronic data storage device and the aforementioned computer.

BACKGROUND

In computer assisted medical procedures such as computer assisted surgery (CAS), instruments are tracked in space via medical tracking systems and, in order for accurately navigating these instruments within a medical environment, need to be calibrated so that the spatial location and orientation of the instrument's functional sections as recognized by the computer precisely corresponds to those sections actual location and orientation.

Instruments and devices are usually calibrated immediately before their use and, for many cases, such initial calibration may be valid throughout an entire medical procedure. For devices and instruments which are adapted to connect to a plurality of objects in an ongoing procedure and are therefore considered as multi-component systems, for example screwdrivers for inserting bone-screws, inserters for inserting artificial joint-components and the like, a calibration procedure needs to be performed many times as the overall geometry of the multi-component system changes with each new system setup and components, implants or screws of the system being added, removed or replaced.

For such cases two major approaches are known in the art: On the one hand, a dedicated calibration procedure is performed each time the overall setup of the system is changed, using a dedicated calibration tool. This not only requires a significant amount of time that adds to the overall duration of treatments, but also distracts medical personnel from their regular activity of treating the patient. Another, more time efficient approach is to replace a dedicated recalibration procedure by a simple user input of new geometric parameters on which basis the navigation system calculates the systems location and orientation. This approach is however prone to errors as there is no true verification whether the input parameters and the system geometry as then recognized by the computer is correct.

The present invention has the object of providing a time efficient but also safe approach for recalibrating a multi-component medical system.

The present invention can be used for any computer assisted medical procedure which needs medical instruments or devices recalibrated in an ongoing medical procedure, e.g. in connection with tracking and navigation systems and software running on computer platforms of such systems for image-guided surgery, such as KICK® or CURVE®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION

In the following, a short description of the specific features of the present invention is given which shall not be understood to limit the invention only to the features or a combination of the features described in this section.

The disclosed method is to update a calibration of a multi-component medical system, wherein a modified spatial relation between a first and a second section of interest of a modified system setup is determined as a function of an initial spatial relation between a first and a second section of interest of an initial setup, particularly wherein at least one component of the initial setup of the medical system may remain in the modified setup of the medical system.

GENERAL DESCRIPTION

In this section, a description of the general features of the present invention is given for example by referring to possible embodiments of the invention.

In general, the invention reaches the aforementioned object by providing, in a first aspect, a computer-implemented medical method of updating a calibration of a multi-component medical system. The method comprises executing, on at least one processor of at least one computer (for example at least one computer being part of a navigation system), the following exemplary steps which are executed by the at least one processor.

In a (for example first) exemplary step initial calibration data is acquired which describes an initial spatial relation between a first section of interest and a second section of interest of an initial setup including one or more components of the medical system.

In a (for example second) exemplary step modification data is acquired which describes a modification of the initial setup of the medical system.

In a (for example third) exemplary step updated calibration data is determined based on the initial calibration data and the modification data, which describes a modified spatial relation between a first section of interest and a second section of interest of a modified setup including one or more components of the medical system, wherein the modified spatial relation is determined as a function of the initial spatial relation, particularly wherein at least one component of the modified setup is included in the initial setup.

In other words, the present approach requires an initial instrument or device calibration performed in a conventional manner known in the art. For example, each component of the multi-part medical system (instrument or device) or the entire system is brought into a predefined spatial relationship with a calibration device. For example, such calibration device may include one or more recesses for inserting the component or the entire instrument with a predefined spatial position and orientation with respect to a tracking marker array of the calibration device. Once the component or the entire instrument has been brought into a predefined spatial position with respect to the calibration device by being inserted into the one or more recesses, the spatial position and orientation of those section of the component or entire instrument within the recesses is therefore also known with respect to the tracking marker array of the calibration device and, in a further step, can be determined with respect to a tracking marker array attached to the component or instrument.

After the initial calibration is complete and the spatial relation between a first section of interest (e.g. a functional instrument portion such as the head of a screwdriver or the tip of a screw engaged by the head of the screwdriver) and a second section of interest (e.g. a tracking marker array of the screwdriver) is determined, a medical procedure can be performed with computer assistance wherein the correct spatial position and orientation of the calibrated component or instrument is recognized by the computer and shown the user, for example on a computer screen, in correct alignment with the patient's anatomy.

Once the medical setup of the multi-component system is modified, for example by engaging a screw with a screwdriver head, by releasing a screw from the screwdriver head or by replacing a screw with a new screw engaged by the screwdriver head, the multi-component system needs to be recalibrated such that its altered geometric properties are known to the computer and are therefore shown on the computer display in a correct location and orientation with respect to the patient's anatomy.

In order to do so, the occurrence of a modification concerning the system setup needs to be recognized by the computer so that a recalibration of the medical system in accordance with the inventive approach described therein can be initiated.

As a full recalibration of the medical system in several dimensions/degrees of freedom and/or for each one of a plurality of system components regularly requires a significant amount of time to be carried out, the present invention suggests to reduce the scope of a recalibration to those components of the modified system setup, which were not included in the initial setup, whereas the calibration for components of the initial system setup which remain in the modified system setup is adopted from the initial calibration. Thus, as the calibration of the modified setup at least partially includes the calibration of the initial setup, the spatial relation between the sections of interest of the modified setup is determined as a function of the spatial relation of the initial setup.

As an illustrative example, the initial setup includes a screwdriver as the only system component, wherein the spatial position and/or orientation of the screwdriver-head with respect to a tracking marker array attached to the screwdriver handle is determined in an initial calibration procedure: Bringing the screwdriver-head into engagement with the head of a screw is considered a modification of the medical system as it now includes, in addition to the screwdriver, a screw coupled to the screwdriver. As the spatial relation between the screwdriver-head and the marker array of the screwdriver remains unamended, a recalibration of the modified system merely needs to consider the geometric properties of the screw added to the system, wherein the calibration data for the screwdriver can be adopted from the initial calibration. Thus, the spatial relation between the screw tip and the screwdriver's marker array can be determined by simply adding the length of the screw to the length of the screwdriver shaft the position and orientation of which is already known with respect to the marker array. In the same manner, replacing that screw with another screw having a different length merely requires determining the new screw length or the difference between the lengths of the screws, respectively.

The general inventive concept can of course be adapted to multi-component systems comprising more than two components. For example, the screwdriver may comprise, as a first component, a handle with a shaft attached thereto, wherein a second component is formed by a screwdriver head releasably attached to the screwdriver shaft (also referred to as screwdriver bit) such that it can be replaced by another screwdriver head having a different geometry and/or a different "blade" for engaging a different screw head. A third component may then be formed by a screw, such that the screwdriver head forms sort of an intermediate component between the screw and the screwdriver. Further, it is also conceivable that a first instrument component such as a handle may connect to a tracking reference array, i.e. a second component, at various sections thereof. Thus, different spatial arrangements of these components with respect to each other define different setups of the multicomponent system.

Of course, the inventive concept can also be adapted to any arbitrary multi-component system having sections of interest the position and orientation of which needs to be known during a medical procedure, for example inserters for inserting implants such as intervertebral implants and vertebral body replacement implants for spinal surgery, or any artificial joint implants, for example for hip or knee replacement surgery.

In a more specific example, the initial calibration data describes a spatial relation between a first section of interest and a second section of interest of at least one, particularly of each component of the initial setup. Further, the updated calibration data may describe a spatial relation between a first section of interest and a second section of interest of at least one, particularly of each component of the modified setup.

In a further example, the modification of the initial setup includes at least one of an alteration of geometric properties of at least one component;

an addition of at least one component;

a removal of at least one component;

a replacement of at least one component by another component.

In other words, the initial system setup may be replaced with the modified system setup by changing a geometry of one or more system components, for example, a plastic deformation of one or more components. Further, as was already described above, adding or removing at least one system component to or from the system may also be considered a modification of the system, for example by connecting or releasing an implant to or from an inserter for deploying that implant. Replacing one component by another component may also be considered a modification of the system, for example when a series of implants with different geometries, for example bone screws having different lengths or diameters, are subsequently introduced into the patient's body by using the same screwdriver.

In a further example, acquiring modification data involves acquiring occurrence data describing an occurrence of the modification via a manual input from an operator; and/or an analysis of image data received from at least one camera adapted to observe the medical system;

indicating that a modification of the initial setup of the medical system has occurred.

For example, the computer may recognize the occurrence of a system modification when such modification is indicated by a surgeon via a manual input on a man-machine-interface of a medical navigation system. Moreover, the occurrence of a modification may also be indicated automatically, for example via a camera system facing towards the medical system. As soon as an image analysis of the camera images shows that the medical system has been modified, for example by recognizing that structures which move in accordance with a tracking marker array assigned to the system have their geometry altered, have been added to the system and/or have been removed from the system, a recalibration may be automatically initiated, or its necessity may at least be indicated to a surgeon operating the system. Further, a recalibration may also be automatically initiated or its necessity be indicated in accordance with other parameters, for example the start or end of certain workflow-steps to be carried out during a medical procedure, the current usage of the medical system within a medical procedure or the position of a medical system within the medical workplace. Such additional parameters may be acquired via a medical tracking system or a medical navigation system assigned thereto, or via a manual input received from a surgeon operating the multi-component medical system.

In order to reduce the time and effort required for recalibration to a necessary minimum, the modification data may describe, particularly exclusively describe a spatial relation between a first section of interest and a second section of interest of at least one, particularly of each component of the modified setup which was not included in the initial setup; and/or a geometric property of which has been altered as compared to the initial setup.

Thus, only those parameters are determined during the recalibration which cannot be adapted from the initial setup.

According to a further example of the present invention, the modification data is acquired from a database including data describing the spatial relation between a first section of interest and a second section of interest of one or more components of the medical system; and/or via an analysis of image data received from at least one camera, particularly from the at least one camera adapted to observe the medical system and/or wherein operator guidance is output to establish at least one spatial position of the medical system with respect to the at least one camera allowing for a sufficient image analysis.

In other words, the initial calibration can be supplemented and/or parts of it can be replaced by data retrieved from a database that includes geometry data of those components that have been added to the medical system. In particular, choosing the correct component from a list of components contained in the database may be based on a manual input of an operator, but may also be based on or at least be supported by an analysis of images received from the camera. For example, the correct type of screw may be chosen from the database based on the comparison of geometric properties (e.g. shaft length, shaft diameter, head geometry, thread pitch) as identified in one or more images received from the camera with corresponding properties assigned to of screw types available in the database. For improving the identification of geometric properties in camera images, an operator may be instructed via an output on a man-machine-interface to position the medical system or at least the component of interest with respect to the camera in a favorable manner, e.g. if a screw length is to be determined, that screw should be best positioned with its longitudinal axis extending perpendicularly to the camera's line of sight.

In a further example, the data required for recalibrating the system may be further reduced if, for at least one component of the modified setup, updated calibration data is determined only for parameters of the modified spatial relation which have been altered as compared to the initial setup. For example, if multiple screws subsequently connected to the screwdriver only differ in their length, other geometric parameters such as the head geometry or the screw diameter may remain unrecognized.

As was already indicated above, the first section of interest may include at least one tracking marker of the medical system, which is adapted to be recognized by a tracking system for determining the spatial position of the medical system. Further, the second section of interest may include a functional portion of the medical system, which is particularly adapted to act upon a patient's anatomy and/or to interact with another functional portion of the medical system.

While the first section of interest and the second section of interest may be assigned to one and the same system component (e.g. the head and the marker array of a screwdriver) those sections may also be assigned to different components of the medical system, which are in particular releasably coupled to each other (e.g. tip of a screw which is, via a screwdriver head and a screwdriver shaft, releasably coupled to the marker array of the screwdriver).

As was also indicated further above, the medical system comprises, particularly as a first component, at least one handle portion adapted to applying force and/or torque on a medical tool or medical implant, and particularly as a second component, at least one medical tool or medical implant, respectively. In other words, the inventive concept can be adapted to tools comprising a plurality of components coupled to each other, which for example may be used to cut soft tissue, drill or drill into bone tissue, as well as to any inserter instrument which are used to introduce medical implants into the patient's body.

In a second aspect, the invention is directed to a computer program comprising instructions which, when the program is executed by at least one computer, causes the at least one computer to carry out method according to the first aspect. The invention may alternatively or additionally relate to a physical carrier carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the fourth aspect;

b) at least one electronic data storage device storing at least the initial calibration data; and c) a medical tracking system for carrying out a medical procedure on the patient, wherein the at least one computer is operably coupled to the at least one electronic data storage device for acquiring, from the at least one data storage device, at least the initial calibration data, and the medical tracking system for issuing a control signal to the medical tracking system for controlling the operation of the medical tracking system on the basis of the updated calibration data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

The present invention also relates to the use of the device/system or any embodiment thereof for conducting a medical procedure. The use comprises for example at least one of the steps according to the first aspect.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium which represents the program, for example the aforementioned program, which for example comprises code means which are adapted to perform any or all of the method steps described herein. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device).

Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information.

Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data; a detection device for detecting the position of the main and auxiliary points in order to generate the absolute point data and to supply the absolute point data to the computer; a data interface for receiving the relative point data and for supplying the relative point data to the computer; and a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
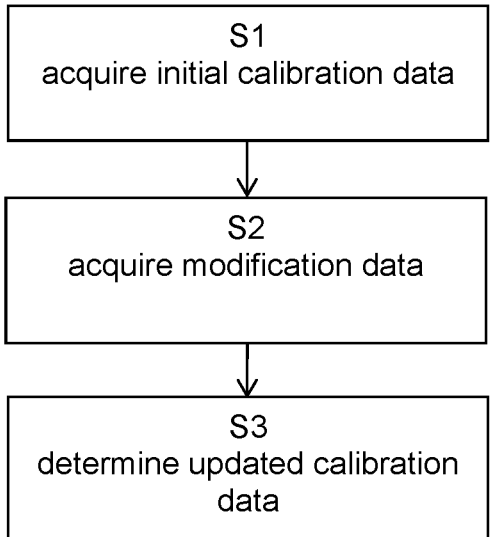
FIG. 1 illustrates the basic steps of the method according to the first aspect.

FIG. 1 illustrates the basic steps of the method according to the first aspect, in which step S1 encompasses acquiring initial calibration data, step S2 encompasses acquiring modification data and subsequent step S3 encompasses determining updated calibration data.

Figure 2:
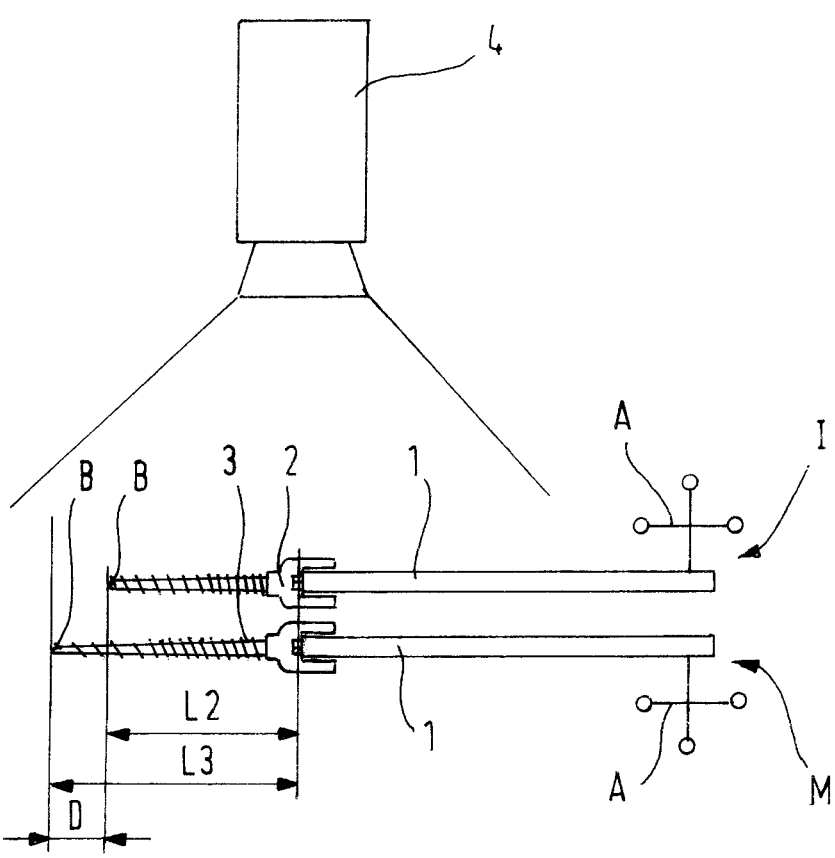
FIG. 2 shows an embodiment of the present invention.

FIG. 2 illustrates a multi-component medical system that may need to be recalibrated during a medical procedure and includes, as system components, a medical screwdriver 1 and a pedicle screw 2 having a length L2. Screw 3 having a different length L3 may be connected to the screwdriver 1 as replacement of screw 2.

In an initial calibration procedure, the spatial relation between the tip B of screw 2 to the marker array A of screwdriver 1 is determined, such that a medical navigation system is able to calculate the correct spatial position of screw tip B within a medical workspace based on the spatial position of marker array A which is determined via a medical tracking system.

By replacing screw 2 by screw 3 the medical system is modified with the result that the spatial relation of tip B of screw 3 to marker array A differs from the spatial relation between tip B of screw 2 with respect to marker array A. In this specific example, the corresponding screw lengths L2 and L3 differ by the amount of D. This difference will be recognized by an analysis of images received from camera 4, such that a recalibration procedure is initiated.

In this specific example, the modified setup M includes screwdriver 1 which already formed part of the initial setup I and, according to the present invention, does not need to be recalibrated. Thus, the recalibration procedure may be reduced to the only parameter of the modified setup M which differs with respect to the initial setup I, i.e. length L3 of screw 3. The correct length of screw 3 may be determined via an analysis of camera images received from camera 4, which may also be used to track the spatial position of the medical system via marker array A. As the spatial position of the longitudinal axis of screwdriver 1 with respect to camera 4 is known from tracking data, length L3 of screw 3 can be calculated based on that data.

The modified setup M of the medical system is therefore recalibrated by simply replacing the screw length L2 by screw length L3. Navigating the medical system can then be easily based on the spatial relation of tip B of screw 3 with respect to the marker array 4 without the need of a full and time-consuming recalibration of the medical system.

Figure 3:
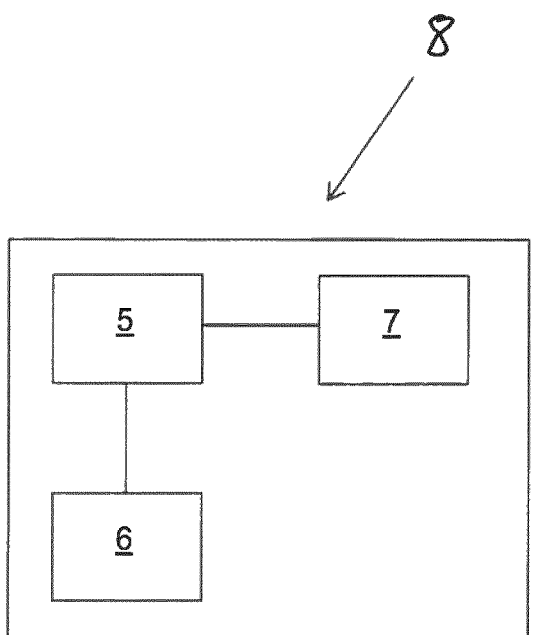
FIG. 3 is a schematic illustration of the system according to the fifth aspect.

FIG. 3 is a schematic illustration of the medical system 8 according to the fifth aspect. The system is in its entirety identified by reference sign 8 and comprises a computer 5, an electronic data storage device (such as a hard disc) 6 for storing at least the patient data and a medical device 7 (such as a radiation treatment apparatus). The components of the medical system 8 have the functionalities and properties explained above with regard to the fifth aspect of this disclosure.

The invention claimed is:

1. A computer-implemented medical method of updating a calibration of a multi-component medical system, the method comprising:

acquiring initial calibration data that describes an initial spatial relation between a first section of interest and a second section of interest of each component of an initial setup including two or more components of the multi-component medical system, wherein:

a first section of interest of a first component includes at least one tracking marker configured to be recognized by a tracking system;

a second section of interest of the first component and a first section of interest of a second component includes functional portions configured to releasably connect to each other; and a second section of interest of the second component includes a functional portion configured to interact with a patient's anatomy and/or another functional portion of the multi-component medical system;

acquiring modification data that describes a modification of the initial setup of the multi-component medical system by adding, removing or replacing the second component by another component; and determining updated calibration data based on the initial calibration data and the modification data, wherein the updated calibration data describes a modified spatial relation between the first section of interest of the first component and the second section of interest of the first component or of the second component of a modified setup of the multi-component medical system, wherein for each component of the initial setup that remains in the modified setup, the spatial relation between the first section of interest and the second section of interest is adopted from the initial calibration data.

2. The method according to claim 1, wherein the modification of the initial setup comprises:

an alteration of geometric properties of at least one component.

3. The method according to claim 1, wherein the acquiring the modification data comprises acquiring occurrence data describing an occurrence of the modification via:

a manual input from an operator; and/or an analysis of image data received from at least one camera adapted to observe the multi-component medical system;

indicating that a modification of the initial setup of the multi-component medical system has occurred.

4. The method according to claim 1, wherein the acquiring the modification data comprises acquiring modification data that describes a spatial relation between the first section of interest and the second section of interest of each component of the modified setup:

that was not included in the initial setup; and/or a geometric property of which has been altered as compared to the initial setup.

5. The method according to claim 1, wherein the acquiring the modification data comprises:

acquiring the modification data from a database including data describing the spatial relation between the first section of interest and the second section of interest of one or more components of the multi-component medical system; and/or acquiring the modification data via an analysis of image data received from at least one camera adapted to observe the multi-component medical system and/or wherein operator guidance is output to establish at least one spatial position of the multi-component medical system with respect to the at least one camera allowing for a sufficient image analysis.

6. The method according to claim 1 further comprising, for at least one component of the modified setup, determining updated calibration data only for parameters of the modified spatial relation that have been altered as compared to the initial setup.

7. The method according to claim 1, wherein the acquiring the initial calibration data comprises acquiring initial calibration data for a first component of the multi-component medical system comprising at least one handle portion adapted to apply force and/or torque on a medical tool or medical implant and, for a second component of the multi-component medical system comprising at least one medical tool or medical implant, respectively.

8. A non-transitory computer readable storage medium storing a computer program comprising instructions that when executed by a computer, cause the computer to update a calibration of a multi-component medical system by:

acquiring initial calibration data that describes an initial spatial relation between a first section of interest and a second section of interest of each component of an initial setup including two or more components of the multi-component medical system, wherein:

a first section of interest of a first component includes at least one tracking marker configured to be recognized by a tracking system;

a second section of interest of the first component and a first section of interest of a second component includes functional portions configured to releasably connect to each other; and a second section of interest of the second component includes a functional portion configured to interact with a patient's anatomy and/or another functional portion of the multi-component medical system;

acquiring modification data that describes a modification of the initial setup of the multi-component medical system by adding, removing or replacing the second component by another component; and determining updated calibration data based on the initial calibration data and the modification data, wherein the updated calibration data describes a modified spatial relation between the first section of interest of the first component and the second section of interest of eachthe first component or of the second component of a modified setup of the multi-component medical system, wherein for each component of the initial setup that remains in the modified setup, the spatial relation between the first section of interest and the second section of interest is adopted from the initial calibration data.

9. A medical system, comprising:

at least one computer comprising at least one processor and a non-transitory computer readable storage medium storing a computer program comprising instructions that when executed by the at least one computer, cause the at least one computer to update a calibration of a multi-component medical system including first and second components by:

acquiring initial calibration data that describes an initial spatial relation between a first section of interest and a second section of interest of each component of an initial setup including two or more components of the multi-component medical system, wherein:

a first section of interest of the first component includes at least one tracking marker configured to be recognized by a tracking system;

a second section of interest of the first component and a first section of interest of the second component includes functional portions configured to releasably connect to each other; and a second section of interest of the second component includes a functional portion configured to interact with a patient's anatomy and/or another functional portion of the multi-component medical system;

acquiring modification data that describes a modification of the initial setup of the multi-component medical system by adding, removing or replacing the second component by another component; and determining updated calibration data based on the initial calibration data and the modification data, wherein the updated calibration data describes a modified spatial relation between the first section of interest of the first component and the second section of interest of the first component or of the second component of a modified setup of the multi-component medical system releasably coupled to each other, wherein for each component of the initial setup that remains in the modified setup, the spatial relation between the first section of interest and the second section of interest is adopted from the initial calibration data;

at least one electronic data storage device storing at least the initial calibration data; and a medical navigation system operable to carry out a medical procedure on the patient, wherein the at least one computer is operably coupled to:

the at least one electronic data storage device for acquiring, from the at least one data storage device, at least the initial calibration data, and the medical navigation system for issuing a control signal to the medical navigation system for controlling the operation of the medical navigation system on the basis of the updated calibration data.

\* \* \* \* \*